United States Patent [19]
Yoshino et al.

[11] 4,000,176
[45] Dec. 28, 1976

[54] PROCESS FOR SIMULTANEOUSLY PRODUCING METHACRYLO-NITRILE AND BUTADIENE BY VAPOR-PHASE CATALYTIC OXIDATION OF MIXED BUTENES

[75] Inventors: Takachika Yoshino, Yokohama; Shigeru Saito, Fuchu; Masukuni Sobukawa, Yokohama; Jun Ishikura, Yokohama; Yutaka Sasaki, Yokohama, all of Japan

[73] Assignee: Nitto Chemical Industry Co., Ltd., Tokyo, Japan

[22] Filed: May 5, 1971

[21] Appl. No.: 140,595

[30] Foreign Application Priority Data

May 18, 1970 Japan .............. 45-41630
Feb. 20, 1971 Japan .............. 46-7741

[52] U.S. Cl. .............. 260/465.3; 260/680 E
[51] Int. Cl.² .............. C07C 120/14; C07C 11/12
[58] Field of Search .............. 260/465.3

[56] References Cited
UNITED STATES PATENTS

| | | | |
|---|---|---|---|
| 3,200,141 | 8/1965 | Milberger | 260/465.3 |
| 3,226,421 | 12/1965 | Giordano et al. | 260/465.3 |
| 3,232,978 | 2/1966 | Yasuhara et al. | 260/465.3 |
| 3,338,952 | 8/1967 | Callahan et al. | 260/465.3 |
| 3,542,843 | 11/1970 | Yoshino et al. | 260/465.3 |

*Primary Examiner*—Joseph P. Brust

[57] ABSTRACT

This invention provides a process for simultaneously producing methacrylonitrile and butdiene which comprises contacting a mixture of mixed butenes containing isobutene and n-butenes, oxygen and ammonia as the substantial reactants with a catalyst containing as the active component a composition having the empirical formula $Fe_{10}Sb_{5-60}Me_{0.01-10}Te_{0.05-5}X_{0-5}O_{20-225}$ wherein Me is at least one element selected from the group consisting of V, Mo and W and X represents P and/or B in vapor phase.

4 Claims, No Drawings

PROCESS FOR SIMULTANEOUSLY PRODUCING METHACRYLO-NITRILE AND BUTADIENE BY VAPOR-PHASE CATALYTIC OXIDATION OF MIXED BUTENES

BACKGROUND OF THE INVENTION

1. Field of the invention

This invention relates to a process for simultaneously producing methacrylonitrile and butadiene by simultaneously effecting ammoxidation and oxidation of mixed butenes containing as the substantial reactant isobutene and n-butenes in vapor phase.

2. Description of the prior art

Heretofore, efficient simultaneous production of methacrylonitrile and butadiene from mixed butenes containing isobutene and n-butenes by simultaneously effecting ammoxidation and oxidation in vapor phase has been considered to be difficult due to difference in reactivity between isobutene and n-butenes when conducted using one and the same catalyst under common reaction conditions.

A number of processes have recently been proposed for the production of methacrylonitrile from olefins by vapor-phase ammoxidation as well as for the production of butadiene from olefins by vapor phase catalytic oxidation. However, all of these processes involve separative use of isobutylene or n-butenes alone, and there has never been proposed the process for simultaneously producing methacrylonitrile and butadiene by vapor-phase oxidation of mixed butenes. Isobutene and n-butene are separated and purified usually from the B-B fraction (fraction containing a mixture of butanes, butenes and butadiene, namely, C₄ fraction) formed on cracking a petroleum fraction (for example, naphtha or kerosene, or crude oil) or the B-B fraction by-produced in purification of petroleum, and isobutene, 1-butene, cis-2-butene, trans-2-butene and butanes are quite similar in chemical and physical properties. Accordingly, separation and purification to isolate isobutene or n-butenes with a high purity are not easy but are expensive.

SUMMARY OF THE INVENTION

The primary object of this invention is to provide a process for simultaneously and efficiently producing methacrylonitrile and butadiene by subjecting a mixture of a mixed butene containing isobutene and n-butenes, air or oxygen and ammonia as the substantial reactants.

The object is realized by the discovery that catalysts consisting of an oxide composition containing iron, antimony, and at least one metal selected from the group consisting of vanadium, molybdenum and tungsten and tellurium, or an oxidation composition consisting of the former composition with oxides of phosphorus and/or boron added exert excellent activities to effect simultaneous production of methacrylonitrile and butadiene in high selectivity at high total conversion and have a long catalyst life.

According to the process of this invention, reactions with a high total conversion of mixed butenes can be carried out at a relatively low temperature and, moreover, simultaneous production of methacrylonitrile and butadiene is feasible under the reaction condition as such at very high conversions. In addition, the methacrylonitrile can suprisingly be obtained in a higher yield than in the production of methacrylonitrile singly from isobutene. The yield of butadiene in this reaction is also no less than that in the vapor phase catalytic oxidation of n-butene alone.

Thus, the present invention provides advantageous execution of vapor phase oxidation reaction of mixed butenes containing isobutene and n-butenes by the use of a specific metal oxide catalyst.

Butanes, if any, are inactive in this reaction in the reaction zone according to the process of this reaction. The presence of ammonia produces no adverse effects in the reaction zone according to the process of this invention. In these respects, the B—B fraction formed on cracking a petroleum fraction such as, for example, naphtha or kerosene or the B—B fraction by-produced in purification of petroleum as it is, or the spent B—B fraction from separation of butadiene from the former fraction can be used as the starting material. As mentioned above, the above is accompanied by great advantages that the reaction with a high total conversion of the B—B fraction is conducted at a relatively low temperature and simultaneous production of methacrylonitrile and butadiene is feasible in a high selectivity. As separation and purfication of the methacrylonitrile and butadiene obtained by the process of this invention are easily conducted by the use of difference in boiling point or solubility in solvent between the two, the process is commercially very advantageous.

Description of the invention

According to the present invention, compositions of the empirical formula

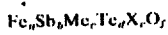

wherein Me is at least one element selected from the group consisting of V, Mo and W, X is P and/or B and the suffixes $a$, $b$, $c$, $d$, $e$ and $f$, respectively denoting the atomic ratio, are of values in the ranges: $5 \leq b \leq 60$, $0.01 \leq c \leq 10$, $0.05 \leq d \leq 5$ and $0 \leq e \leq 5$ when $a=10$ and $f$ is a value corresponding to the oxides formed from the above-mentioned components by combination and is from 20 to 225 are used as the catalyst useful in effecting the simultaneous production of methacrylonitrile and butadiene by vapor-phase oxidation of mixed butenes.

The ratio of iron to antimony in the catalyst of this invention is defined in terms of atomic ratio to be from 10:5 to 10:60. Ratios from 10:10 to 10:60 are preferred. This is critical for good activity as well as for good selectivity with respect to the aforementioned reaction and is determined on the basis of experiments.

The vanadium, molybdenum or tungsten component is preferably added at a ratio from 0.01 to 10 against 10 of the iron component in terms of atomic ratio. As for the tellurium component, it is preferable to add at a ratio from 0.05 to 5 against 10 of the iron component. The phosphorus or boron component is preferably added at a ratio from 0 to 5 against 10 of the iron component.

The catalyst having the above-mentioned composition can be produced by any known method, provided that the components are intimately mixed and combined. Said empirical formula is based upon the analytical value, although exact chemical structure of material constituting the catalyst is unknown.

The starting material for providing the iron component of the catalyst can be selected from many members. For example, an oxide of iron in the form of ferrous oxide, ferric oxide or ferro-ferric oxides can be used. Also, those compounds which are finally stabilized as iron oxide after chemical treatment, calcining treatment or the like may be used. These compounds include salts of iron with an inorganic acid such as iron nitrate and iron chloride, salts of iron with an organic acid such as iron acetate and iron oxalate, etc. The salts can be converted into the oxide by neutralizing them with a basic substance such as aqueous ammonia to form iron hydroxide and then calcining said iron hydroxide or by directly calcining them. Besides, hydroxides of iron or metallic iron can be used. The metallic iron may be added in the form of fine powder or may be treated with heated nitric acid. In the latter case the iron is converted into the ferric nitrate. Whatever starting material is selected, it is critical to intimately mix the material with other components.

The starting material for the antimony component may be metallic antimony powder or antimony oxide such as, for example, antimony trioxide, antimony tetroxide or antimony pentoxide. Also, those compounds which are finally stabilized as antimony oxide after chemical treatment, calcining treatment or the like may be used. For example, these compounds include hydrous antimony oxide, meta-antimonic acid, orthoantimonic acid, pyroantimonic acid or the like. Also, hydrolyzable antimony salts such as antimony halides, for example, antimony trichloride and antimony pentachloride may be used. These antimony halides are hydrolyzed with water into the hydrous oxides. It is preferable not to place these antimony halides directly under calcining treatment as they are volatile at elevated temperature. As in the case of iron component intimate mixing with other compounds is necessary.

Any one of water soluble or insoluble vanadium compounds can be used as the vanadium component source. For example, vanadium pentoxide, ammonium metavanadate, vanadyl oxalate, vanadium halides or the like may be used.

Any one of water soluble or insoluble molybdenum compounds can be used as the molybdenum component source. For example, molybdenum trioxide, molybdic acid, ammonium paramolybdate, ammonium metamolybdate, molybdenum halides or the like may be used.

As for the tungsten component source, the same is applicable as with the molybdenum component source.

As the tellurium component source can be used metallic tellurium powder or any one of water soluble or insoluble tellurium compounds. For instance, tellurium dioxide, tellurous acid or telluric acid may be used.

It is preferable to produce the catalyst composition by intimately mixing the vanadium, molybdenum or tungsten component and the tellurium component together with the iron and antimony components from the beginning. Alternatively, the catalyst may be produced by initially preparing an iron-antimony base catalyst followed by impregnation thereof with other components. In the latter case, an aqueous solution of the above-mentioned components is prepared and then the iron-antimony base catalyst is impregnated in the solution. The impregnation is made preferably prior to the final calcining treatment, if possible.

The phosphorus or boron component may either be coexisting in the aqueous solution of the aforementioned components or may be separately impregnated. The phosphorus or boron component may be of any nature but is most conveniently added in the form of phosphoric acid or boric acid.

Acitivity of this catalyst system is increased by heating the same at a high temperature. The catalyst material composition which has been prepared to provide the desired composition and intimately mixed is dried and then heated at a temperature preferably from 200° to 600° C. for 2 to 24 hours and, if necessary, heated for additional 1 to 48 hours at a temperature in the range of 600° to 1100° C.

The catalyst can show excellent activity even without any carrier, but it may be combined with any suitable carrier. The entire catalyst may be formulated so that it contains 10 to 90 percent by weight of the catalytic composition. As the carrier may be used silica, alumina, zirconia, silica alumina, silicon carbide, alundum, inorganic silicate, etc.

Any other additives such as a binding agent, which serve for improving the physical properties of the catalyst, may be optionally added unless they impair the activity of the catalyst.

The additives such as a carrier, a binding agent, an extender, etc. can be optionally added irrespective of their composition provided that they do not remarkably change the characteristics of the catalyst of the present invention as described in the above or in the examples below. The catalyst containing these additives should be also regarded as the catalyst of the present invention.

The catalyst may be used in a fixed-bed reactor in the form of pellet or may be used in a fluidized-bed reactor in the form of fine particle.

The reaction conditions for the use of the catalyst of the present invention will be explained below.

Any oxygen source may be employed but, for economy, air is conveniently used. On the other hand, space-time yield in the process of this invention can be increased by replacing all or a part of the air by oxygen to increase the concentration of mixed butenes in the reaction gas while maintaining the mixed butenes-oxygen molar ratio in a predetermined range. Under such reaction conditions, yields of the desired products are considerably lowered with the prior-art catalysts, whereas use of the catalyst of this invention is encountered with almost no reduction of the yields. The enrichment of air with oxygen as set forth above is a favorable means for increasing efficiency in the purification system and prolonging the life of the catatyst. The process involving the oxygen enrichment is preferably conducted in a fluidized bed-reactor. The molar ratio of oxygen to mixed butenes is preferably in the range between 0.5 and 6.

The formation of methacrylonitrile requires at least 1 mole of ammonia per mole of isobutene. Lower ratios of ammonia will be unfavorable due to higher by-production of methacrolein. The amount of ammonia used is preferably at a molar ratio from 1 to 6 on the basis of isobutene in the mixed butenes. Composition of the starting gas is variable depending upon the composition of mixed butenes and it is preferred to lower the ratio of oxygen and ammonia with higher content of 1-butene and to raise the ratio of oxygen and ammonia with higher content of isobutene.

Addition of steam to the reaction gas, which is often used in the gas phase catalytic oxidation reaction, may also be introduced in the process of this invention, if required. Use of water in an amount below 5 moles per mole of the mixed butenes may be sufficient in such a case.

An embodiment of the method of supplying the starting gas may be divided supply of oxygen made in such a manner as described in U.S. Pat. No. 3,446,617, which often produces good results. The supply is conveniently made by appropriately providing for a sparger in the same fluidized bed-reactor. The divided charge of pure oxygen is preferred in view of the object and produces good results, but air may also be employed.

Low partial pressure of oxygen will facilitate by-production of methacrolein even if partial pressure of ammonia is sufficiently high. In such a case divided suppply of oxygen is significantly effective for lowering the production of methacrolein.

The presence of ammonia produces no substantial effect upon the oxidative dehydrogenation of n-butenes. In some cases, on the contrary, co-existence of ammonia appears to increase the butadiene selectivity.

The temperature at which the reaction is carried out is suitably in the range between about 350° and 500° C. and the reaction when conducted at a temperature from about 380° to 480° C. produces especially good results. From the operational point of view it is preferable to carry out the reaction at atmospheric pressure but, if required, reduced or elevated pressure may be applied.

Space velocity, which is a critical reaction condition in the vapor phase catalytic reaction, is suitably from about 5000 to 100 hr. $^{-1}$ in the process of this invention. The reaction when conducted at a space velocity from about 2000 to 200 hr.$^{-1}$ produces especially good results. The space velocity referred to herein is the value of gas volume in terms of NTP passing per hour per unit volume of the catalyst.

Recovery of the desired products methacrylonitrile and butadiene from the reaction product may be made by washing the outlet gas from the reactor with cold water or a solvent suitable for extracting methacrylonitrile and butadiene. Also, any method for recovery which is conventional in the reaction of such a nature may be used.

In carrying out the process of this invention any one of the fixed bed-catalyst, moving bed catalyst and fluidized bed-catalyst equipment conventionally used for the gas phase catalytic reaction may be employed.

The catalysts of this invention generally have little ammonia combustibility but some of them with a certain composition have the combustibilities, on which addition of steam is effective for the inhibition.

During the process of this invention 2-butene probably undergoes isomeriztion, which then produces butadiene. As compared with 1-butene, 2-butene is low in reaction rate and slightly inferior in selectivity.

DESCRIPTION OF PREFERRED EMBODIMENTS

Embodiments of the construction and results of the present invention are shown by the following Examples and Reference Examples:

Preparation of the catalyst

Catalyst 1

A catalyst with the empirical formula $Fe_{10}Sb_{25}W_{0.25}Te_{1.0}O_{67.8}(SiO_2)_{30}$ was prepared as follows:

To 225 ml. of hot nitric acid (specific gravity 1.38) were added portionwise 60.9 g. of metallic antimony powders (below 100 mesh). After completion of the addition of antimony and evolution of brown gas, the mixture was allowed to stand at room temperature for 16 hours. The excess nitric acid was removed and precipitates washed with three portions of 100 ml. of water. (I)

To a solution composed of 81 ml. of nitric acid (specific gravity 1.38) and 100 ml. of water were added portionwise 11.2 g. of electrolytic iron powders to a perfect solution. (II)

In 50 ml. of water were dissolved 1.3 g. of ammonium tungstate $[5(NH_4)_2O \cdot 12WO_3 \cdot 5H_2O]$ as described in Merck Index. (III)

To the solution of ammonium tungstate prepared above were added 4.6 g. of telluric acid $H_6TeO_6$ to a solution. (IV)

As the carrier component were employed 180 g. of silica sol ($SiO_2$ 20% by weight). (V)

To a mixture of II and IV was added. The liquid thus prepared was mixed with I. To the resulting mixture under stirring was added portionwise aqueous ammonia to pH 2. The resulting mass was heated under stirring to dryness.

The dried matter, pulverized, was calcined at 200° C. for 2 hours and subsequently at 400° C. for 2 hours, followed by addition of water and blending. The blended matter was formed into pellets 2mm. × 2mm.$\phi$, which was dried at 130° C. for 16 hours and then calcined at 900° C. for 2 hours.

Catalyst 2

A catalyst with the empirical formula $Fe_{10}Sb_{10}W_{0.3}Te_{2.5}O_{40.1}(SiO_2)_{20}$ was prepared in accordance with the formulation of Catalyst 1.

Catalyst 3

A catalyst with the empirical formula $Fe_{10}Sb_{25}V_{0.25}Te_{0.5}O_{66.6}(SiO_2)_{30}$ was prepared in accordance with the formulation of Catalyst 1 except that 0.6 g. of ammonium metavanadate were used in place of 1.3 g. of ammonium tungstate for Catalyst 1.

Catalyst 4

A catalyst of the empirical formula $Fe_{10}Sb_{13}V_{0.07}Te_{0.33}O_{41.8}(SiO_2)_{20}$ was prepared in accordance with the formulation of Catalyst 1 except that ammonium metavanadate and tellurium dioxide were used respectively as the starting materials for the V and Te components.

Catalyst 5

A catalyst with the empirical formula $Fe_{10}Sb_{25}Mo_{0.1}Te_{0.5}O_{66.3}(SiO_2)_{30}$ was prepared in accordance with the formulation of Catalyst 1 except that ammonium molybdate $[(NH_4)_6Mo_7O_{24} \cdot 4H_2O]$ was used in place of the ammonium tungstate.

Catalyst 6

A catalyst with the empirical formula $Fe_{10}Sb_5Mo_{1.5}Te_2O_{34}(SiO_2)_6$ was prepared in accordance with the formulation of Catalyst 1 except that ammonium molybdate was used as the starting material for the Mo component.

Catalyst 7

A catalyst with the empirical formula $Fe_{10}Sb_{10}Mo_2Te_1O_{43}(SiO_2)_{60}$ was prepared in accordance with the method for Catalyst 1 except that ammonium molybdate was used as the starting material for the Mo component.

Catalyst 8

A catalyst with the empirical formula $Fe_{10}Sb_{25}-Mo_5-Te_2O_{64}(SiO_2)_{30}$ was prepared in accordance with the method for Catalyst 1 except that ammonium molybdate was used as the starting material for the Mo component.

Catalyst 9

A catalyst with the empirical formula $Fe_{10}Sb_{50}-Mo_{10}-Te_1O_{147}(SiO_2)_{30}$ was prepared in accordance with the method for Catalyst 1 except that ammonium molybdate was used as the starting material or the Mo component.

Catalyst 10

A catalyst with the empirical formula $Fe_{10}Sb_{25}-Mo_{1.5}Te_2O_{74}(SiO_2)_{60}$ was prepared in accordance with the method for Catalyst 1 except that ammonium molybdate was used as the starting material for the Mo component.

Catalyst 11

A catalyst with the empirical formula $Fe_{10}Sb_{10}Mo_2-Te_1P_1O_{46}(SiO_2)_{60}$ was prepared in accordance with the method for Catalyst 1 except that ammonium molybdate and phosphoric acid were used respectively as the starting materials for the Mo and P components.

Catalyst 12

A catalyst with the empirical formula $Fe_{10}Sb_5-Mo_{1.5}Te_2B_1O_{35}(SiO_2)_{60}$ was prepared in accordance with the method for Catalyst 1 except that ammonium molybdate and boric acid were used respectively as the starting materials for the Mo and B components.

Catalyst 13

A catalyst with the empirical formula $Fe_{10}Sb_5Mo_2-Te_4O_{39}(SiO_2)_{60}$ was prepared in accordance with the method for Catalyst 1 except that ammonium molybdate was used as the Mo component.

Catalyst 14

A catalyst with the empirical formula $Fe_{10}Sb_{15}-Mo_{1.5}Te_2O_{54}(SiO_2)_{60}$ was prepared as follows:

To 7 liters of nitric acid, specific gravity 1.38, heated to about 80° C. were added portionwise 1.83 kg. of metallic antimony powders less 100μ in particle size. After completion of the oxidation of antimony the excess of nitric acid was washed with water, followed by pulverization in a ball mill for 3 hours. (I)

To a mixture of 4 liters of nitric acid, specific gravity 1.38, and 5 liters of water heated to about 80° C. were added 0.56 kg. of electrolytic iron powders to a perfect solution firmly observed.

To the iron nitrate solution prepared above were added portionwise 0.255 kg. of metallic tellurium powders to a perfect solution firmly observed. (II)

In 17.75 kg. of silica sol containing 20% by weight $SiO_2$ were dissolved 0.27 kg. of ammonium molybdate. (III)

I, II and III were mixed and aqueous ammonia (15%) was added to the mixture to adjust the pH to 2. The resulting mixture was heated under stirring at 100° C. for 2 hours.

The slurry thus prepared was spray-dried by a conventional method using a spray-dring apparatus.

The resulting fine spherical particles were gradually heated to a temperature from 500° C. to 600° C. at which temperature heating was continued for 2 hours, followed by calcining at 700° C. for 8 hours.

Catalyst 15

A catalyst with the empirical formula $Fe_{10}Sb_{10}Mo_2-Te_3O_{47}(SiO_2)_{60}$ was prepared in accordance with the method for Catalyst 14.

Catalyst 16

A catalyst with the empirical formula $Fe_{10}Sb_{25}-V_2Te_2O_{74}(SiO_2)_{60}$ was prepared in accordance with the method for Catalyst 1 except that ammonium metavanadate was used as the starting material for the V component.

Catalyst 17

A catalyst with the empirical formula $Fe_{10}Sb_{15}-V_{1.5}Te_2O_{53}(SiO_2)_{60}$ was prepared in accordance with the method for catalyst 1 except that ammonium metavanadate was used as the starting material for the V component.

Catalyst 18

A catalyst with the empirical formula $Fe_{10}Sb_{25}V_4-Te_2P_1O_{92}(SiO_2)_{60}$ was prepared in accordance with the method for Catalyst 1 except that ammonium metavanadate was used as the starting material for the V component and phosphoric acid for the P component.

Catalyst 19

A catalyst with the empirical formula $Fe_{10}Sb_5W_3-Te_2O_{38}(SiO_2)_{60}$ was prepared in accordance with the method for Catalyst 1.

Catalyst 20

A catalyst with the empirical formula $Fe_{10}Sb_{10}W_4-Te_1O_{49}(SiO_2)_{60}$ was prepared in accordance with the method for Catalyst 1.

Catalyst 21

A catalyst with the empirical formula $Fe_{10}Sb_{15}-Mo_1W_1Te_2O_{55}(SiO_2)_{60}$ was prepared in accordance with the method for Catalyst 1 except that ammonium molybdate was used as the starting material for the Mo component.

Catalyst 22

A catalyst with the empirical formula $Fe_{10}Sb_{10}-V_{0.5}W_{1.5}Te_2O_{45}(SiO_2)_{60}$ was prepared in accordance with the method for Catalyst 1 except that ammonium vanadate was used as the starting material for the V component.

Catalyst 23

A catalyst with the empirical formula $Fe_{10}Sb_{15}-O_{45}(SiO_2)_{60}$ was prepared in accordance with the method for Catalyst 1 except that the Te and Me component were not added.

Catalyst 24

A catalyst with the empirical formula $Fe_{10}Sb_{25}-Te_2O_{69}(SiO_2)_{60}$ was prepared in accordance with the method for Catalyst 1 except that the Me component was not added.

Catalyst 25

A catalyst with the empirical formula $Fe_{10}Sb_{10}Mo_{20}Te_2O_{99}(SiO_2)_{60}$ was prepared in accordance with the method for Catalyst 1 except that ammonium molybdate was used as the starting material for the Mo component.

Catalyst 26

A catalyst with the empirical formula $Fe_{10}Sb_{10}Mo_5O_{50}(SiO_2)_{60}$ was prepared in accordance with the method for Catalyst 1 except that ammonium molybdate was used as the starting material for the Mo component and the Te component was not added.

Catalyst 27

A catalyst with the empirical formula $Fe_{10}Sb_{10}V_{15}Te_2O_{77}(SiO_2)_{60}$ was prepared in accordance with the method for Catalyst 1 except that ammonium metavanadate was used as the starting material for the V component.

Catalyst 28

A catalyst with the empirical formula $Fe_{10}Sb_{10}W_{15}Te_2O_{84}(SiO_2)_{60}$ was prepared in accordance with the method for Catalyst 1.

The conditions under which calcining of each of these catalysts was made are shown in Table 1.

Methods and results of the test.

The method of testing the catalyst was as follows:

1. Composition of the mixed butenes starting materials.
   A. Isobutene 52%, 1-butene 48%.
   B. Butane 12%, isobutene 46%, 1-butene 47%.
   C. Butane 5%, isobutene 48%, 1-butene 47%.

The starting material used are cited in the table as A, B or C.

2. Reaction procedures.
2-1. Reaction in a fixed bed

Reactions were performed in a fixed bed using Catalysts 1-13 and 16-28.

A U-shaped reactor, 16 mm.$\phi$ in inner diameter and 500 mm. in length, was filled with 15 ml. of the catalyst with Catalysts 1-5 or 20 ml. of the catalyst with other catalysts. The reactor was heated in a salt bath of an equal-amount mixture of sodium nitrite and potassium nitrate to maintain the same at a predetermined reaction temperature. The reactant gas was passed through the reactor thus prepared at a rate of 15 liters per hour (in termin of NTP) with Catalysts 1-5 or 10 liters per hour with other catalysts. The reaction pressure was atmospheric.

Composition of the supplied gas was as follows:
1. With Catalysts 1-5.
   $O_2$ (supplied in the form of air)/mixed butenes = 3.5 (molar ratio)
   $NH_3$/mixed butenes = 1.3 (molar ratio)
   $H_2O$/mixed butenes = 3.5 (molar ratio)
2. With other catalysts.
   $O_2$ (supplied in the form of air)/mixed butenes = 3.4 (molar ratio)
   $NH_3$/mixed butenes = 0.8 (molar ratio)

The bath temperature was successively changed and reaction was continued for 30 min. to 1 hour at a given temperature. The reaction gas was analyzed by gas chromatography. Data of the reactions that have given the best results are shown in Table 1.

2-2. Reaction in a fluidized bed (air process).

Reactions were performed in a fluidized bed using Catalysts 14 and 15.

The reaction apparatus used was 2 in. in inner diameter and 1 m. in height. It was filled with the catalyst 10-100$\mu$ in particle size for the most part in such a manner that space velocity was 1,000 hr.$^{-1}$ The supplied gas prepared so as to give the below-mentioned composition was passed through the reactor at a linear velocity of 15 cm./sec.

$O_2$ (supplied in the form of air)/mixed butenes = 2.9 (molar ratio) ammonia/mixed butenes = 0.8 (molar ratio)

Analysis of the reaction gas was made by gas chromatography.

Results of the reactions are shown in Table 1.

2-3. Reaction in a fluidized bed (oxygen process).

Reactions were performed in a fluidized bed using Catalysts 14 and 15.

The reaction apparatus was identical with one under 2—2, which was filled with the catalyst in such a manner that space velocity was 1,000 hr.$^{-1}$ Removal of heat was then facilitated by simultaneously putting inactive fine spherical particles composed of such as silica having almost the same physical properties as those of the catalyst in the same amount by volume as that of the catalyst.

The reaction gas prepared so as to give the below-mentioned composition was passed through the reactor at a linear velocity of 15 cm./sec.

$O_2$ (pure oxygen for industrial use)/mixed butenes = (molar ratio)

$NH_3$/mixed butenes = 0.8 (molar ratio)

In the reaction column was set a sparger at the position corresponding to about 1/3 the total contact time, from which 2/5 the amount of the inlet supplied oxygen was charged.

Analysis of the reaction was made by gas chromatography.

Results of the reactions are shown in Table 2.

In addition, in order to demonstrate that the catalyst according to this invention maintain the activity under conditions suitable for practical procedure over a long period of time results of a reaction operated for a long period of time are shown in Table 3.

Reaction conditions were the same as in the case using Catalysts 14 and 15 under 2—2.

The total conversion respectively of isobutene and n-butenes (1-butene and 2-butene) in the mixed butenes and conversion respectively to methacrylonitrile and butadiene as referred to herein are defined as follows:

Total conversion (%) of isobutene A $$= \frac{\text{Weight of the carbon in isobutene reacted}}{\text{Weight of the carbon in isobutene supplied}} \times 100$$

Total conversion (%) of n-butenes B $$= \frac{\text{Weight of the carbon in n-butenes reacted}}{\text{Weight of the carbon in n-butenes supplied}} \times 100$$

Conversion (%) to methacrylonitrile A'

$$= \frac{\text{Weight of the carbon in methacrylonitrile formed}}{\text{Weight of the carbon in isobutene supplied}} \times 100$$

Conversion (%) to butadiene B'

$$= \frac{\text{Weight of the carbon in butadiene formed}}{\text{Weight of the carbon in n-butenes supplied}} \times 100$$

Selectivity (%) of methacrylonitrile = A'/A × 100
Selectivity (%) of butadiene = B'/B × 100

Reference Example

Using Catalyst 1 aforementioned, 1-butene or isobutene alone was subjected to vapor phase catalytic oxidation under the conditions 1 or 2 set forth below to determine the optimum temperature at which the maximum conversion to butadiene or methacrylonitrile was achieved and the conversion and selectivity at the same temperature. Results are summarized in Table 4.

| Condition 1. | Amount of the catalyst 20 ml. Total amount of the gas 10 Nl./hr. $O_2$ (supplied in the form of air)/1-butene & = 1.0 (molar ratio) & $H_2O$/butenes = 1.5 (molar ratio) |
|---|---|
| Condition 2. | Amount of the catalyst 15 ml. Total amount of the gas 15 Nl./hr. $O_2$ (supplied in the form of air)/isobutene & = 3.5 (molar ratio) & $NH_3$/isobutene = 3.5 (molar ratio) $H_2O$/isobutene = 4.0 (molar ratio) |

Table 1

| Example | Catalyst | Fe | Sb | Composition of the catalyst (atomic ratio) Me | Te | X | Si | Temp. (°C) | Hour (hrs) | Mixed butenes starting material |
|---|---|---|---|---|---|---|---|---|---|---|
| & 1 | & 1 | 10 | 25 | W 0.25 | 1 | 0 | 30 | 900 | 2 | A |
| 2 | 2 | 10 | 10 | W 0.03 | 2.5 | 0 | 20 | 925 | 2 | C |
| 3 | 3 | 10 | 25 | V 0.25 | 0.5 | 0 | 30 | 925 | 2 | A |
| 4 | 4 | 10 | 13 | V 0.07 | 0.33 | 0 | 20 | 925 | 2 | C |
| 5 | 5 | 10 | 25 | Mo 0.1 | 0.5 | 0 | 30 | 900 | 2 | A |
| 6 | 6 | 10 | 5 | Mo 1.5 | 2 | 0 | 60 | 720 | 4 | A |
| 7 | 7 | 10 | 10 | Mo 2 | 1 | 0 | 60 | 700 | 4 | A |
| 8 | 8 | 10 | 25 | Mo 5 | 2 | 0 | 30 | 700 | 4 | A |
| 9 | 9 | 10 | 50 | Mo 10 | 1 | 0 | 30 | 650 | 4 | B |
| 10 | 10 | 10 | 25 | Mo 1.5 | 2 | 0 | 60 | 750 | 4 | B |
| 11 | 11 | 10 | 10 | Mo 2 | 1 | P 1 | 60 | 710 | 4 | B |
| 12 | 12 | 10 | 5 | Mo 1.5 | 2 | B 1 | 60 | 720 | 4 | B |
| 13 | 13 | 10 | 5 | Mo 2 | 4 | 0 | 60 | 650 | 4 | A |
| 14 | 14 | 10 | 15 | Mo 1.5 | 2 | 0 | 60 | 700 | 8 | A |
| 15 | 15 | 10 | 10 | Mo 2 | 3 | 0 | 60 | 700 | 8 | A |
| 16 | 16 | 10 | 25 | V 2 | 2 | 0 | 60 | 700 | 4 | A |
| 17 | 17 | 10 | 15 | V 1.5 | 2 | 0 | 60 | 750 | 4 | A |
| 18 | 18 | 10 | 25 | V 4 | 2 | P 1 | 60 | 650 | 4 | A |
| 19 | 19 | 10 | 5 | W 3 | 2 | 0 | 60 | 750 | 4 | A |
| 20 | 20 | 10 | 10 | W 4 | 1 | 0 | 60 | 750 | 4 | A |
| 21 | 21 | 10 | 15 | Mo 1 W 1 | 2 | 0 | 60 | 700 | 4 | A |
| 22 | 22 | 10 | 10 | V 0.5 W 1.5 | 2 | 0 | 60 | 800 | 4 | A |
| & Reference Example |  |  |  |  |  |  |  |  |  |  |
| & 1 | 23 | 10 | 15 | 0 | 0 | 0 | 60 | 850 | 4 | A |
| 2 | 24 | 10 | 25 | 0 | 2 | 0 | 60 | 600 | 4 | A |
| 3 | 25 | 10 | 10 | Mo 20 | 2 | 0 | 60 | 650 | 4 | A |
| 4 | 26 | 10 | 10 | Mo 5 | 0 | 0 | 60 | 650 | 4 | A |
| 5 | 27 | 10 | 10 | V 15 | 2 | 0 | 60 | 600 | 4 | A |
| 6 | 28 | 10 | 10 | W 15 | 2 | 0 | 60 | 700 | 4 | A |

| Example | Optimum reaction temperature (°C) | Total conversion (%) of Isobutene | Total conversion (%) of 1-butene, 2-butene | Conversion (%) to Methacrylonitrile | Conversion (%) to Butadiene | Selectivity (%) Methacrylonitrile | Selectivity (%) Butadiene |
|---|---|---|---|---|---|---|---|
| & 1 | 435 | 98 | 93 | 76 | 83 | 78 | 89 |
| 2 | 430 | 98 | 92 | 75 | 80 | 77 | 87 |
| 3 | 440 | 98 | 93 | 75 | 81 | 77 | 87 |
| 4 | 430 | 97 | 89 | 73 | 78 | 75 | 88 |
| 5 | 430 | 98 | 89 | 75 | 79 | 77 | 89 |
| 6 | 430 | 98 | 90 | 70 | 77 | 71 | 86 |
| 7 | 430 | 95 | 89 | 73 | 74 | 77 | 83 |
| 8 | 420 | 96 | 92 | 74 | 80 | 77 | 87 |
| 9 | 430 | 95 | 87 | 69 | 72 | 73 | 83 |
| 10 | 410 | 94 | 88 | 73 | 75 | 78 | 85 |
| 11 | 420 | 93 | 86 | 75 | 72 | 81 | 84 |
| 12 | 420 | 92 | 87 | 71 | 75 | 77 | 86 |
| 13 | 430 | 94 | 89 | 72 | 77 | 77 | 86 |
| 14 | 430 | 98 | 94 | 83 | 84 | 85 | 89 |
| 15 | 410 | 96 | 93 | 81 | 82 | 85 | 88 |

Table 1-continued

| | | | | | | | |
|---|---|---|---|---|---|---|---|
| 16 | 400 | 99 | 97 | 68 | 71 | 69 | 73 |
| 17 | 400 | 98 | 96 | 62 | 65 | 63 | 68 |
| 18 | 400 | 93 | 90 | 58 | 60 | 62 | 67 |
| 19 | 410 | 94 | 91 | 63 | 70 | 67 | 77 |
| 20 | 400 | 98 | 95 | 60 | 66 | 61 | 70 |
| 21 | 410 | 99 | 98 | 66 | 69 | 67 | 70 |
| 22 | 400 | 96 | 93 | 70 | 71 | 73 | 76 |
| & Reference Example | | | | | | | |
| & 1 | 420 | 81 | 80 | 47 | 50 | 58 | 63 |
| 2 | 430 | 91 | 90 | 52 | 55 | 57 | 61 |
| 3 | 410 | 92 | 88 | 20 | 60 | 22 | 68 |
| 4 | 400 | 90 | 86 | 30 | 63 | 33 | 73 |
| 5 | 410 | 91 | 87 | 18 | 41 | 20 | 47 |
| 6 | 410 | 88 | 85 | 32 | 51 | 36 | 60 |

Table 2

| Example | Catalyst | Composition of the catalyst (atomic ratio) | | | | | Mixed butenes starting material | Optimum reaction temperature (°C) | Total conversion (%) of | | Conversion (%) to | | Selectivity (%) | |
|---|---|---|---|---|---|---|---|---|---|---|---|---|---|---|
| | | Fe | Sb | Mo | Te | Si | | | Iso-butene | 1-butene, 2-butene | Methacrylonitrile | Butadiene | Methacrylonitrile | Butadiene |
| 23 | 14 | 10 | 15 | 1.5 | 2 | 60 | A | 420 | 100 | 96 | 80 | 83 | 80 | 86 |
| 24 | 15 | 10 | 10 | 2 | 3 | 60 | B | 400 | 99 | 93 | 78 | 80 | 79 | 86 |

Table 3

| Example | Catalyst | Composition of the catalyst (atomic ratio) | | | | | Mixed butenes starting material | Optimum reaction temperature (°C) | Elapsed time (hour) | Total conversion (%) of | | Conversion (%) to | | Selectivity (%) | |
|---|---|---|---|---|---|---|---|---|---|---|---|---|---|---|---|
| | | Fe | Sb | Mo | Te | Si | | | | Iso-butene | 1-butene, 2-butene | Methacrylonitrile | Butadiene | Methacrylonitrile | Butadiene |
| 25 | 14 | 10 | 15 | 1.5 | 2 | 60 | A | 430 | 1 | 98 | 94 | 83 | 84 | 85 | 89 |
| | | | | | | | | | 5 | 97 | 94 | 83 | 83 | 86 | 88 |
| | | | | | | | | | 10 | 98 | 94 | 84 | 84 | 86 | 89 |

Table 4

| Butene starting material | Optimum reaction temperature (°C) | Total conversion of 1-butene (%) | Conversion to butadiene (%) | Selectivity to butadiene (%) | Total conversion of isobutene (%) | Conversion to methacrylonitrile (%) | Selectivity to methacrylonitrile (%) |
|---|---|---|---|---|---|---|---|
| 1-Butene | 430 | 90 | 79 | 88 | — | — | — |
| Iso-butene | 420 | — | — | — | 98 | 67 | 68 |

We claim:

1. Process for simultaneously producing methacrylonitrile and butadiene which comprises contacting a mixture of mixed butenes consisting essentially of isobutene and n-butenes, oxygen and ammonia in the vapor phase at a temperature within the range from 350° to 500° C., and at a space velocity of said mixture within the range from about 5000 to 100 per hour and at an oxygen/mixed butene molar ratio from 0.5/1 to 6/1 and an ammonia/isobutene molar ratio from 1/1 to 6/1 with a catalyst containing as the active component a composition having the empirical formula

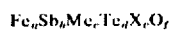

wherein Me is at least one element selected from the group consisting of vanadium, molybdenum and tungsten, X is at least one element selected from the group consisting of boron and phosphorous and, when $a=10$, $5 \leq b \leq 60$, $0.01 \leq c \leq 10$, $0.05 \leq d \leq 5$, $0 \leq e \leq 5$ and $f$ is a number in the range 20–225.

2. Process according to claim 1 wherein said catalyst is activated by calcining at a temperature within the range from 600° to 1100° C. for 1–48 hours prior to use.

3. Process according to claim 1 wherein said catalyst is in combination with a silica carrier in an amount from 10 to 90% by weight.

4. Process according to claim 1 wherein said catalyst is activated by heat treatment at a temperature within the range from 200° to 600° C. for 2–24 hours and then heated at a temperature within the range from 600° to 1100° C. for 1–48 hours.

UNITED STATES PATENT OFFICE
CERTIFICATE OF CORRECTION

PATENT NO. : 4,000,176
DATED : December 28, 1976
INVENTOR(S) : Takachika Yoshino, et al.

It is certified that error appears in the above-identified patent and that said Letters Patent are hereby corrected as shown below:

Col. 6, line 33, "$W_{0.3}$" should read as --$W_{0.03}$--

Col. 7, line 15, "or" should read as --for--

Col. 7, line 53, after the word "acid", the following was omitted --was removed and the antimony oxidized with nitric acid--

Col. 8, line 15, after $SiO_2$ insert ")"

Col. 9, line 35, "47%" should read as --28%, 2-butene 14%--

Signed and Sealed this

Twenty-ninth Day of March 1977

[SEAL]

Attest:

RUTH C. MASON
*Attesting Officer*

C. MARSHALL DANN
*Commissioner of Patents and Trademarks*